US009125783B2

(12) United States Patent
Doak (10) Patent No.: US 9,125,783 B2
(45) Date of Patent: Sep. 8, 2015

(54) PORTABLE SURGICAL PLATFORM (71) Applicant: Morzine Medical, LLC, Atlanta, GA (US)

(72) Inventor: John H. Doak, Baltimore, MD (US)

(73) Assignee: Morzine Medical, LLC, Atlanta, GA (US)

( * ) Notice: Subject to any disclaimer, the term of this patent is extended or adjusted under 35 U.S.C. 154(b) by 0 days.

(21) Appl. No.: 14/337,051

(22) Filed: Jul. 21, 2014

(65) Prior Publication Data

US 2015/0040319 A1 Feb. 12, 2015

Related U.S. Application Data (60) Provisional application No. 61/856,898, filed on Jul. 22, 2013.

(51) Int. Cl.
| A61G 1/06 | (2006.01) |
| A61G 13/10 | (2006.01) |
| A61G 1/02 | (2006.01) |
| A61G 13/04 | (2006.01) |
| A61G 13/12 | (2006.01) |
| A61M 5/14 | (2006.01) |
| A61G 1/052 | (2006.01) |

(52) U.S. Cl.
CPC ............ *A61G 13/105* (2013.01); *A61G 1/0293* (2013.01); *A61G 13/04* (2013.01); *A61G 13/101* (2013.01); *A61G 13/104* (2013.01); *A61G 13/1235* (2013.01); *A61M 5/1414* (2013.01); *A61G 1/052* (2013.01)

(58) Field of Classification Search
CPC ......... A61G 1/00; A61G 1/0293; A61G 1/06; A61G 13/105
USPC ............. 5/620, 625–629, 110–118, 174–180; 108/50.1, 50.01, 115; 182/152
See application file for complete search history.

(56) References Cited

U.S. PATENT DOCUMENTS

| 2,133,692 | A | * | 10/1938 | Gittings et al. .................... 5/627 |
| 2,722,690 | A | * | 11/1955 | Donargo ............................... 5/8 |
| 2,757,386 | A | * | 8/1956 | Lappin .................................. 5/8 |
| 3,046,072 | A | * | 7/1962 | Douglass, Jr. et al. ............ 5/646 |
| 3,104,401 | A | * | 9/1963 | Davis .................................. 5/627 |
| 3,336,060 | A | * | 8/1967 | Bradford ....................... 403/108 |
| 3,359,576 | A | * | 12/1967 | Pile .................................. 5/111 |
| 5,375,276 | A | * | 12/1994 | Nelson et al. .................... 5/620 |
| 6,142,491 | A |   | 11/2000 | Darling |
| 6,164,671 | A |   | 12/2000 | Darling |
| 6,546,577 | B1 | * | 4/2003 | Chinn .............................. 5/600 |

(Continued)

*Primary Examiner* — Michael Trettel
(74) *Attorney, Agent, or Firm* — Miller & Martin, PLLC (57) ABSTRACT A folding, lightweight, portable, and rugged surgical operating platform apparatus that can be erected quickly under adverse conditions at any location and without tools other than the users hands and without the need to attach any loose pieces to form the unitary platform. As needed, the surgical platform will hold, support, elevate, move, and tilt a stretcher (or litter in military terms) bearing a wounded person and the portable surgical support equipment such as IV poles, surgical instrument trays, armboards, wrist restraints, leg stirrups, light poles, and other equipment that a surgeon needs to treat major injuries and save lives. In the folded position, the platform takes up limited, uniform space for ease of portability by a single individual. Different users have different applications and requirements for how the platform is supported using stationary supporting legs or wheels when rolling capability are required.

25 Claims, 7 Drawing Sheets

(56) References Cited

U.S. PATENT DOCUMENTS

| | | |
|---|---|---|
| 2008/0276372 A1 | 11/2008 | Lambarth |
| 2009/0165207 A1 | 7/2009 | Reed et al. |
| 2009/0260159 A1* | 10/2009 | Buchanan ......................... 5/617 |
| 2009/0300844 A1 | 12/2009 | Taylor |
| 2011/0277242 A1 | 11/2011 | Dionne et al. |

* cited by examiner

PORTABLE SURGICAL PLATFORM

CROSS-REFERENCE TO RELATED APPLICATIONS

The present application claims priority to and the benefit of the filing date of U.S. Provisional Patent Application Ser. No. 61/856,898 filed Jul. 22, 2013, which is incorporated herein by reference.

BACKGROUND OF THE INVENTION

The present invention relates to an apparatus to be used in the provision of medical services, particularly surgical procedures within adverse field environments.

When a person suffers a major injury, the immediate next hour is the "Golden Hour" in that the medical treatment received in the first sixty minutes to stabilize the injury and prevent further complications is usually critical in preventing loss of life or limb.

For soldiers, sailors, and airmen injured in battle, the initial medical treatment is usually "care under fire" provided by a medic or Navy corpsman as close as possible to the time and place of injury with whatever medical equipment the medic or corpsman carries on their person. The medic or corpsman's critical task is to stabilize the wound and assist in getting the wounded soldier to the nearest medical facility where doctors and surgeons provide more extensive treatment of the wound and stabilization of the wounded soldier before transferring them to a hospital.

In modern warfare, military doctors and/or forward surgical treatment units are located even closer to the battlefield to stabilize major wounds and save soldiers' lives as soon as possible after the time of injury. In Iraq and Afghanistan today, this often means a surgeon operating on a wounded soldier in a house, hotel, commercial building, tent, or even in the open at or near the time and place of injury. For a surgeon to work effectively on wounded soldiers under such conditions and save as many soldiers' lives as possible, the surgeon needs a platform to hold the stretcher (or litter in military terms) on which the wounded soldier is brought to them. This platform would function as an operating table in a hospital in raising or lowering the patient to whatever height the surgeon requires, tilting the stretcher as needed for various medical procedures, and supporting required equipment such as intravenous poles, surgical instrument trays, lights, patient arm boards, stirrups for lower extremity wounds, and other surgical equipment.

Thus it can be seen that there is a need for this means a portable, light-weight operating platform that can be carried by one person and erected quickly under adverse conditions at any location to allow surgeons to treat the wounded soldier as quickly and effectively as possible to stabilize their wounds and save their life.

A similar need exists in the non-military world in situations of mass casualties in natural or man-made disasters. Under normal situations when a civilian suffers major injury, they can be rushed by ambulance or helicopter to a nearby hospital for emergency shock trauma treatment. However, in the event of a mass casualty, roads can be impassable, local hospitals can be overwhelmed, and medical evacuation helicopters insufficient by the sheer number of injured people. In non-military mass casualty disasters as in warfare, the need is for a portable, light-weight operating table or platform than can be carried by one person and erected quickly under adverse conditions at any location to allow surgeons to treat critically injured people as quickly and effectively as possible to stabilize wounds and save lives.

Another critical problem and need is in the event of biological or chemical attack or "spill." In this situation, hospitals with formal operating rooms in close proximity may be available, but to prevent contamination of hospitals and surgical operating theaters it will almost certainly be necessary to perform life-saving surgical procedures in a variety of buildings, tents, or other facilities away from the hospitals and other patient treatment facilities.

The objective of the present invention is to provide a novel apparatus for a portable, light-weight operating platform that can be carried by one person and erected quickly under adverse conditions at any location.

BRIEF SUMMARY OF THE INVENTION

Among the several objects of this invention may be noted the provision of an apparatus for, as described and shown herein, a folding, lightweight, portable, and rugged surgical operating platform that can be erected quickly, in one embodiment in less than one minute, under adverse conditions at any location and without tools. The basic platform includes no loose pieces that would require assembly or risk being lost in the field. In one embodiment, the platform weighs approximately thirty-four pounds and the platform and its parts and attachments can be folded up to dimensions of approximately 41 inches by 12 inches by 15 inches so that it can be carried by one person. It will hold, support, elevate, move, and tilt as needed a stretcher carrying a wounded person weighing well in excess of at least 400 pounds, including any desired portable surgical support equipment such as IV poles, surgical instrument trays, armboards, wrist restraints, leg stirrups, light poles, and other equipment that a surgeon needs to treat major injuries and save lives. For example, the platform is designed to allow IV poles to be mounted into all four corners of the platform and the platform side rails accept all surgical table accessories that mount on $5/16$ inch by $1\frac{1}{8}$ inch rails. In the medical field, rail mounted accessories are designed to be compatible with standard rails with these measurements as such the side rails provided will accommodate most standard accessories.

The platform provides a stable platform for surgery in a wide variety of emergencies and other situations where in-hospital surgical facilities are not readily available. Different users have different applications and requirements for how the platform is supported using the support members, which are outward-canted to provide strength and stability, such as whether or not wheels and rolling capability are required. For some users the need for ultimate lightweight portability combined with maximum platform stability dictates rigid mounted legs, and wheels and rolling capability are not required in such embodiments. In other embodiments, rigid mounted legs can be switched to wheels or vice versa without tools in less than 10 seconds per leg. Where mobility is required, mounting holes in the rigid mounted legs are drilled off-center so that when mounted on the outward-canted support members, caster spindles are vertical so that the casters function properly.

The height of the stretcher may, in one embodiment, be adjusted from 28 inches to 36 inches without tools to meet the surgeon's preference by moving the yolk arms up or down with the locking pin. The legs are individually adjustable, such that the platform can be height-adjusted and tilted from end to end, with up to about a 15 inch change in elevation from end to end. Likewise, legs may be adjusted from side to side if on a sloping surface. Preferably, adjustments may be made in less than five seconds using the mounting knob. Having the ability to tilt the platform from side-to-side toward the surgeon makes it easier for a surgeon to work on a wounded soldier or injured person without having to lean over the platform, and should reduce surgeon physical fatigue in day-long mass casualty situations.

In a preferred embodiment, all swiveling, sliding, and folding aluminum connections between structural elements are separated by ultra-low coefficient of friction virgin polytetrafluoroethylene (or Teflon®) or ultra-high-molecular-weight (UHMW) polyethylene spacers to prevent aluminum self-galling and seizing of mating surfaces, incorporate oil-impregnated bronze bushings, and are held together with stainless steel bolts and deformed-thread self-locking nuts tightened to prevent play.

BRIEF DESCRIPTION OF THE DRAWINGS

The particular features and advantages of the invention as well as other objects will become apparent from the following description taken in connection with the accompanying drawings in which.

DETAILED DESCRIPTION OF THE INVENTION

Figure 1:
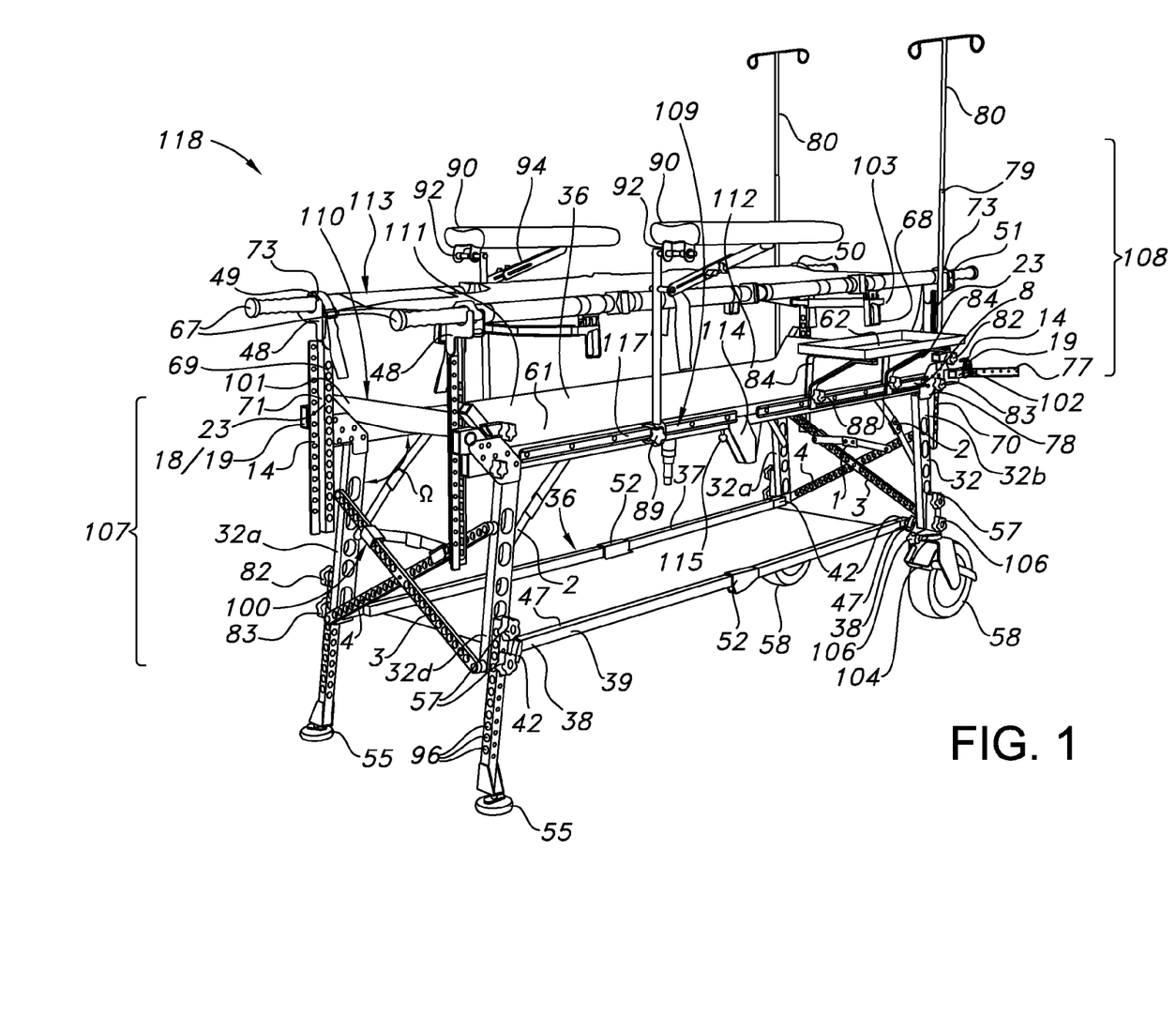
FIG. 1 is a side perspective view of an embodiment of a portable surgical platform according to the present invention in an unfolded, operational configuration carrying a litter in a substantially level position.

FIG. 1 is a side perspective view of one embodiment of a portable field surgical platform 118 according to the present invention in an unfolded, operational configuration. Portable surgical platform 118 comprises a rigid support structure, such as a pair of collapsible sides, such as elongated horizontal beams 109, 110 (parallel horizontal beam 110 shown better in FIG. 4), supported by a plurality of support members 32 connected to and supporting the horizontal beams. The plurality of support members 32 are preferably arranged in corresponding, opposing pairs 32a-32b, and 32c-32d spaced apart along the length of the substantially parallel horizontal beams 109, 110.

When the platform 118 is erected for use, opposing pairs of support members 32a-32b, and 32c-32d are preferably connected to and rigidly braced apart by a pair of folding, pivotably connected cross-bars 3, 4, said cross-bars 3, 4 held rigidly in place by means of a two piece locking brace 2 connected at either end to both of the cross-bars 3, 4, the two pieces of the locking brace 2 joined together, such as by a connecting link 1. Connecting link 1 may be pulled to straighten the two pieces of the locking brace 2 between the cross-bars 3, 4. The cross-bars 3, 4 connect to opposing support members 32 at either end, thereby connecting each pair of support members 32a-32b and 32c-32d together and acting as a brace to force the support members 32 apart and maintain the horizontal beams 109, 110 substantially in parallel when the platform 118 is assembled for operation.

Figure 2:
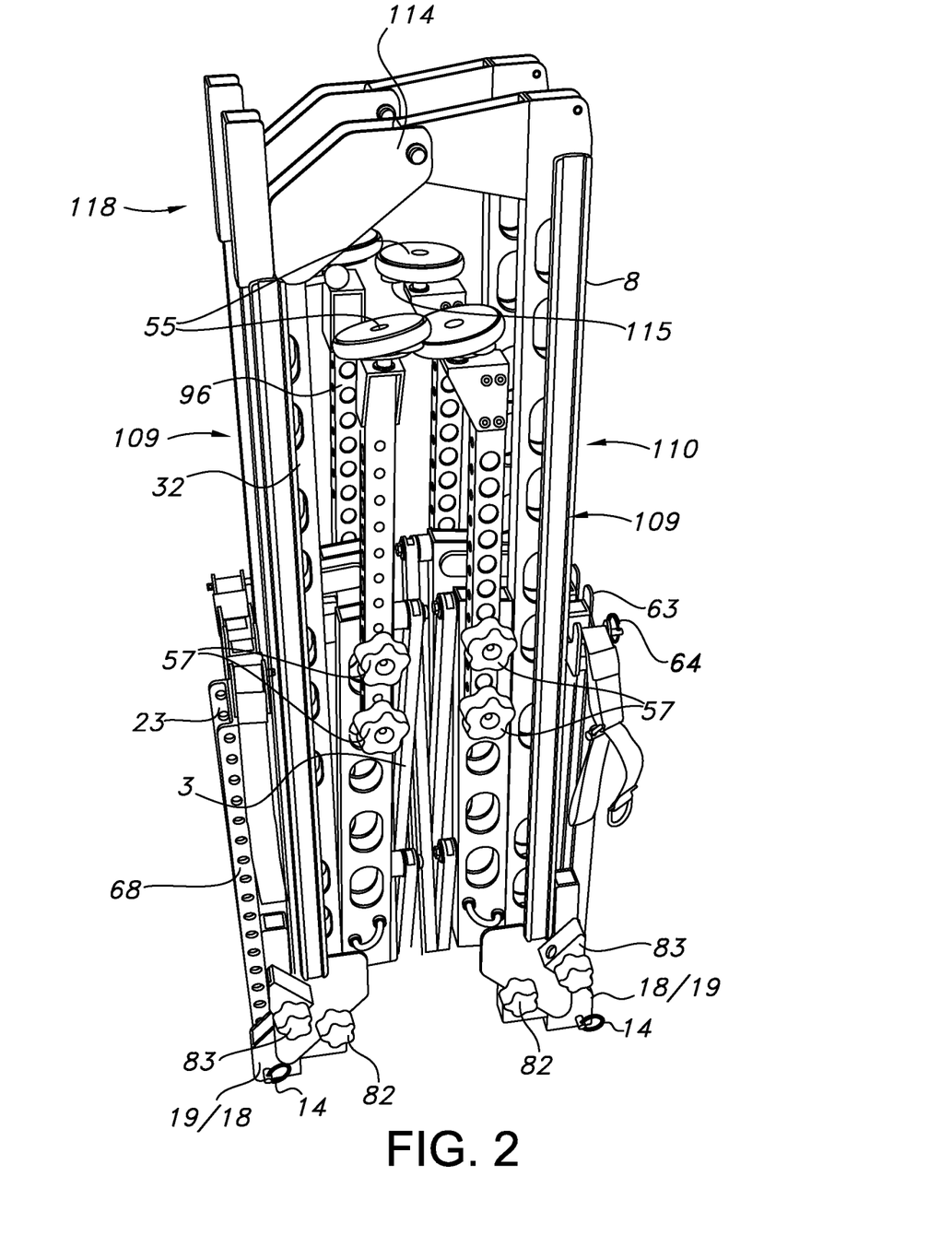
FIG. 2 is a side perspective view of a portable surgical platform according to the present invention in a fully folded, upright configuration.

The horizontal beams 109, 110 are both comprised of two or more submembers 111, 112, such as a first submember and second submember, each submember having an inboard and outboard end, connected by a pivoting hinge 114 that is held rigidly in either an open or unfolded position (shown in FIG. 1) or a folded position (shown in FIG. 2) by a locking means, such as a locking knob 115 or pins or other suitable means. When the platform 118 is unfolded and in its assembled configuration for operation, the pivoting hinge 114 allows the inboard ends of the submembers 111, 112 to meet and align such that submembers 111, 112 are substantially coplanar and form substantially straight horizontal beams 109, 110. As shown in FIG. 2, when the platform 118 is folded into its folded or carrying configuration, pivoting hinge 114 allows submembers 111, 112 to lie substantially parallel to each other, and defines an internal space between the submembers 111, 112, leaving room into which the support members 32 may also be folded substantially parallel to the submembers 111, 112.

Returning to FIG. 1, when in operational position, the submembers 111, 112 of horizontal beams 109, 110 are substantially parallel and are axially aligned, i.e. have a common or substantially common longitudinal axis. In one embodiment, the pivoting hinge 114 is configurable to lock in the folded position, the unfolded operational position, or, preferably, both. The locking means 115 can be automatic, e.g. spring loaded, or manual. In another preferred embodiment, the pivoting hinge 114 is configured to lock automatically in the operational position via releasable internal spring loaded hooks. In one embodiment, releasable, manual latching clamps may be suitably used, such latching clamps (not shown) having a mechanical stop to prevent any unwanted reversal of the mechanism under strain, which locks the submembers 111, 112 in position relative to each other.

Figure 5:
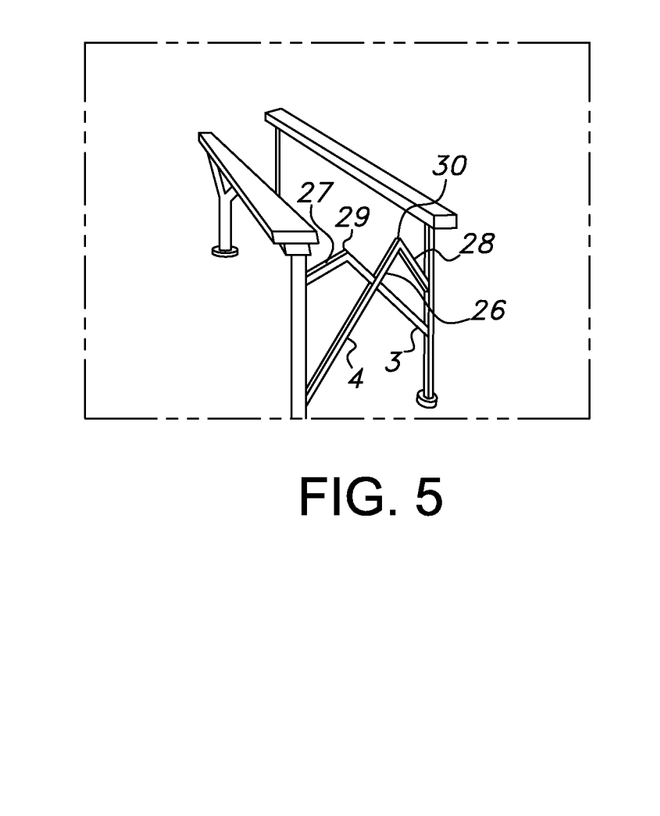
FIG. 5 is an end perspective view of a portable field surgical platform according to the present invention in a partially unfolder configuration.
Figure 6:
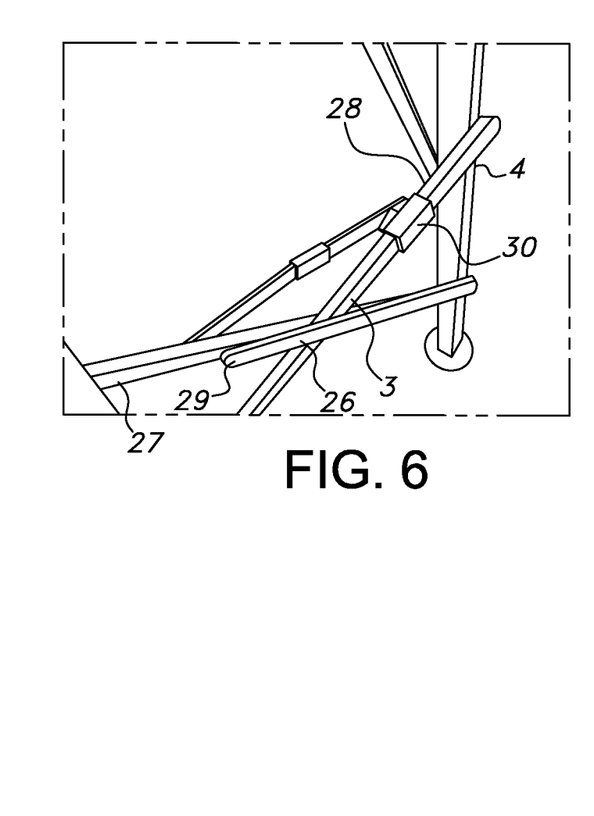
FIG. 6 is a detailed perspective view of the folding cross-bars between the support members and the locking brace of an embodiment of the portable surgical platform.

As shown in FIGS. 5 and 6, the "scissor" action of the pivotably-connected cross-bars 3, 4 between the support members 32 allows the platform 118 to unfold for operational use, maintaining the beams 109, 110 in parallel, and fold for carrying without the use tools (other than the users hands) or the need to connect any loose pieces to form the unitary platform 118. Cross-bars 3, 4 are connected at a centrally-located pivot point 26. Portions 27, 28 of the cross-bars 3, 4, are also have a hinge point 29, 30 to allow the opposing pairs of support members 32a-32b, and 32c-32d, to be pushed together inwardly, collapsing the cross-bars 3, 4 until, as shown in FIG. 2, the cross-bars 3, 4 lie substantially parallel with each other and with the support members 32 and submembers 111, 112 of the beams 109, 110.

In one embodiment, an untrained person can erect the platform from the folded up stage to the operational position ready to receive the stretcher, and with only minimal instruction, the surgical platform of the present invention may be erected from the fully folded, carrying position to the operational position in about 60 seconds or less.

As shown in FIG. 6, each support member 32 is unfolded and locked in position with cross-bars 3, 4. To provide additional stability, a two-piece locking brace 2 and connecting link 1 are provided to brace the support members 32 apart. In one preferred embodiment, the outer opposing ends of the locking brace 2 are connected at the hinge point 29, 30 of the portions 27, 28 of the cross-bars 3, 4. Connecting link 1 may be pulled to straighten the two pieces of the locking brace 2 between the cross-bars 3, 4. Preferably, connecting link 1 is snugly snap fit about the locking brace when in the straightened, locking position, but may be unsnapped by hand when the platform 118 is to be folded.

When locked in position, support members 32a-32b and 32c-32d are canted outward away from each other from the opposing ends 107, 108 of the platform 118. Support members 32a-32b and 32c-32d are preferably positioned at an angle $\Omega$ relative to the submember to which it is hingedly connected, said angle being greater than 90 degrees, but less than about 105 degrees from the corresponding submember 111, 112, which range includes all values and subranges therebetween. In the preferred embodiment shown in FIG. 1, the individual support members 32a-32b and 32c-32d and submembers 111, 112, 98, 99 (shown in FIG. 4) to which it is connected are locked at an angle, for the operational position, at an angle $\Omega$ of about 95 degrees relative to one another. This has the desirable result that pushing the platform 118 from one end will not allow the support members 32 to fold up because the outward slant of the support member 32 causes the platform 118 to lift rather than the support members 32 fold inward. As such, the heavier load on the platform 118, the greater the resistance to the platform support members 32a, 32b, 32c, 32d inadvertently folding up.

A two piece locking brace 2 having a connecting link 1 is connected between the individual support members 32a, 32b, 32c, 32d and the outboard end of its corresponding submember 111, 112, 98, 99. Of course, alternate locking means (not shown), such as a tightening knob or pin, may be provided at the joint or pivot point at which a support member 32a, 32b, 32c, 32d is connected to its corresponding submember 111, 112, 98, 99.

Figure 3:
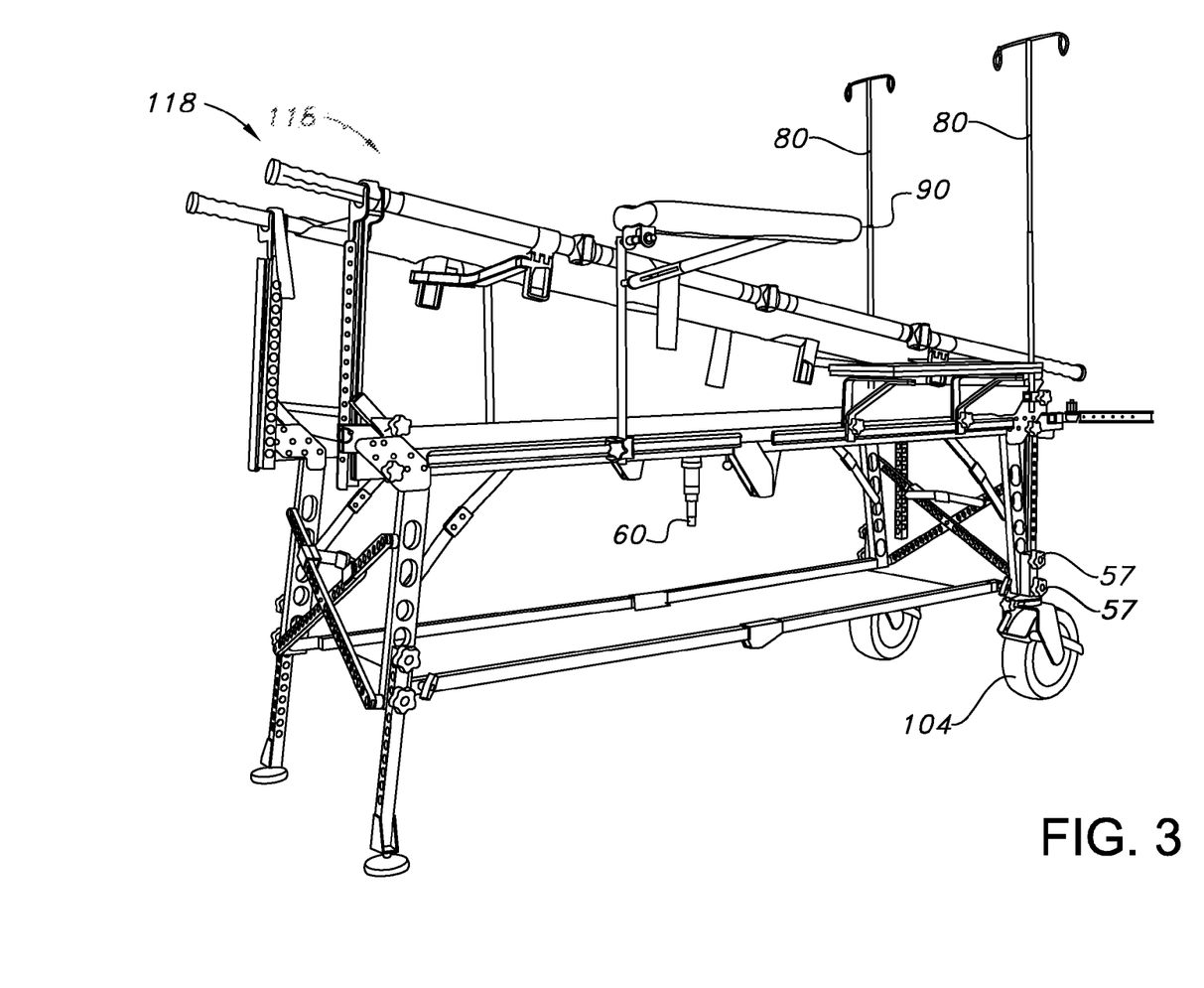
FIG. 3 is a side perspective view of the portable surgical platform of FIG. 1 in an unfolded operational configuration carrying a litter in the "Trendelenburg" position.

As shown in FIG. 1, support members 32 may be adapted to receive an interchangeable base, such as non-skid, self-leveling feet 55, wheels 58, casters (not shown), or a combination thereof. For example, all or only two of the support members 32 may have self-leveling feet 55, or all or only two of the support members 32 may have wheels 58. In the embodiment shown in FIG. 1, the two support members 32a, 32b at one end of the platform 118 have wheels 58 affixed, and the two support members 32c, 32d at the opposing end have self-leveling legs 55 affixed to allow the platform 118 to be moved by a single individual from one end like a wheelbarrow. In the alternate embodiment shown in FIG. 4, non-skid, self-leveling feet 55 have been affixed to all support members 32.

Where wheels 58 are desired, as best shown in FIG. 3, they may be mounted to the support members 32 by means of a releasable connecting device, such as a mounting knob 57. Wheels 58 may also comprise a break, such as foot-operated break lever 104, and a swivel lock, such as locking knob 106, or other control mechanism. Wheels 58 may be formed from any suitable material, but to achieve the desired reduction in weight, the wheels 58 are preferably constructed of expanded foam.

Figure 4:
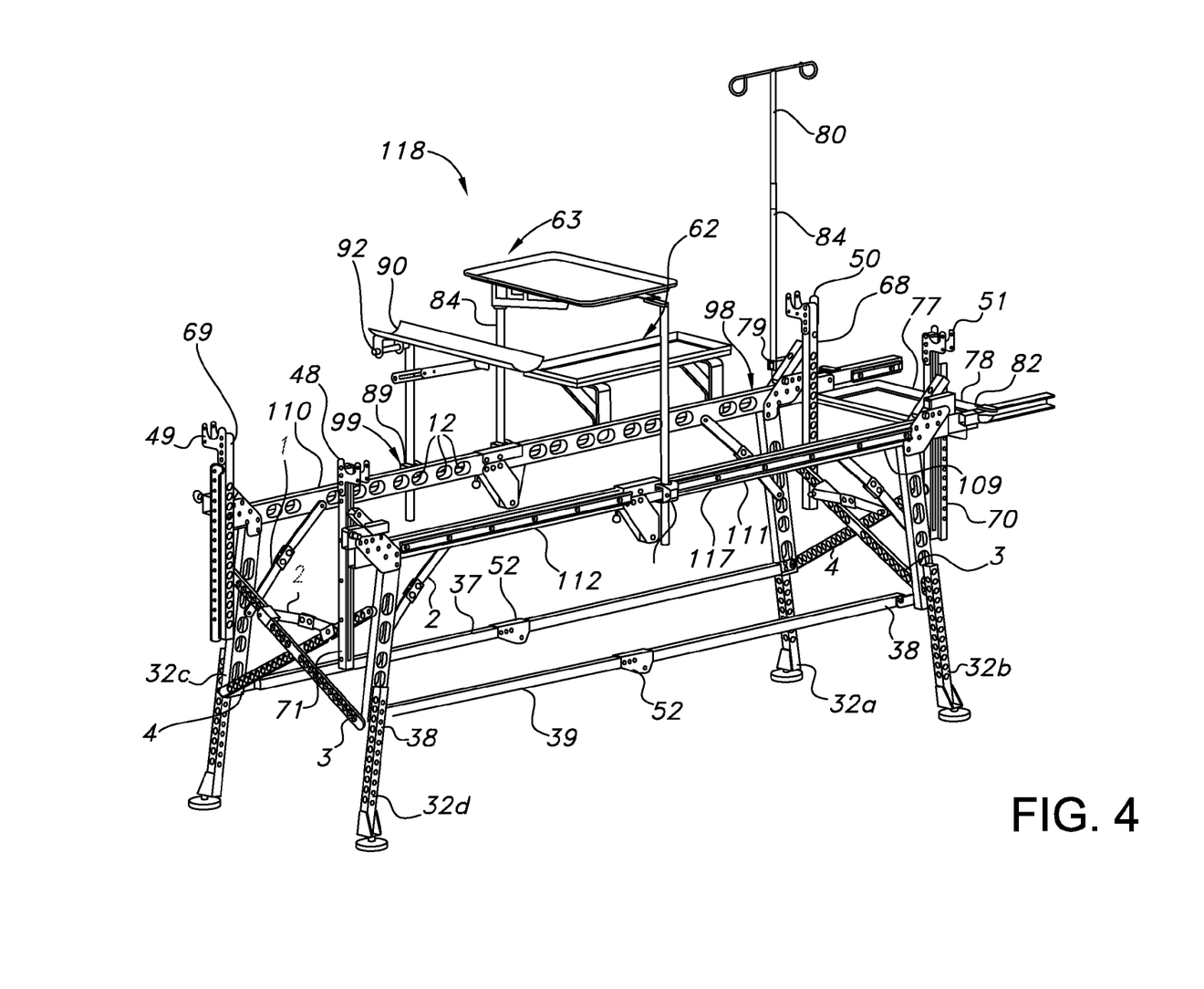
FIG. 4 is a side perspective view of another embodiment of the portable surgical platform of the present invention in an operational configuration showing the attachment of a number of optional, standard operating table attachments.

In a preferred embodiment best shown in FIG. 4, support members 32 further comprise leg extensions 43, 44, 45, 46 which may be used to adjust the length of support members 32 (and thus the height of the platform 118) as desired.

Figure 7:
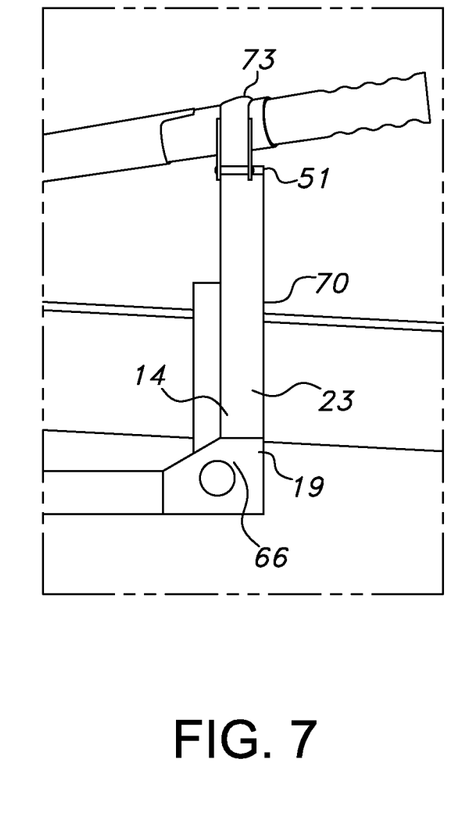
FIG. 7 is a detailed perspective view of a yoke and yoke arm of a portable surgical platform according to the present invention having a stretcher pole of the litter secured to the yoke.

Connected to the platform 118 proximate to each corner 100, 101, 102, 103 of the platform 118 is a yoke 48, 49, 50, 51 to adapted to receive the litter or stretcher poles 67 and lock the stretcher 113 to the platform 118. In the preferred embodiment, a yoke 48, 49, 50, 51 is carried upon a corresponding yoke arm 68, 69, 70, 71 which is pivotably attached proximate to each outboard or distal end of the horizontal beams 109, 110 so that the yoke arm 68, 69, 70, 71 may be pivoted to a first position flat, lengthwise along the beam 109, 110 when the platform 118 is in the folded position, or pivoted to a second position substantially perpendicular to the beam 109, 110 when the platform 118 is unfolded to the operational position. As best illustrated in FIG. 7, which is a close-up view of yoke 51, yoke arm 70, yoke arm hinge 66, and a distal end of beam 109, a yoke arm hinge 66 provides the pivot point for the attachment of yoke arm 70 and is configured so that the yoke arm 70 may only be pivoted when the end of the yoke arm 70 attached to the yoke 51 is fully extended away from the pivot point inside yoke arm hinge 66. When the yoke arm 70 is pivoted to the second, perpendicular position relative to the beam 109, the yoke arm 70 may then be adjusted by raising and lowering it vertically, to adjust the height of the yoke 51 relative to the beam 109.

Figure 8:
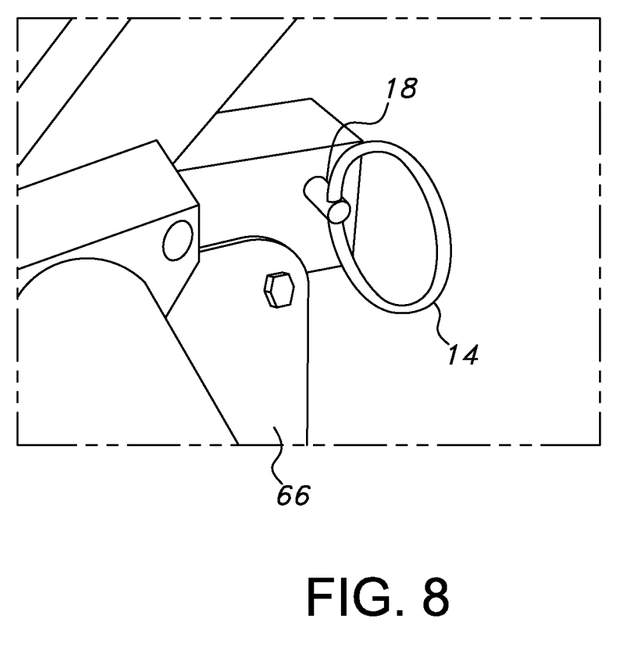
FIG. 8 is a detailed perspective view of a yoke arm housing about a yoke arm wherein the spring-loaded pin is positioned within the yoke arm housing in a first vertical position to prevent movement of the yoke arm.
Figure 9:
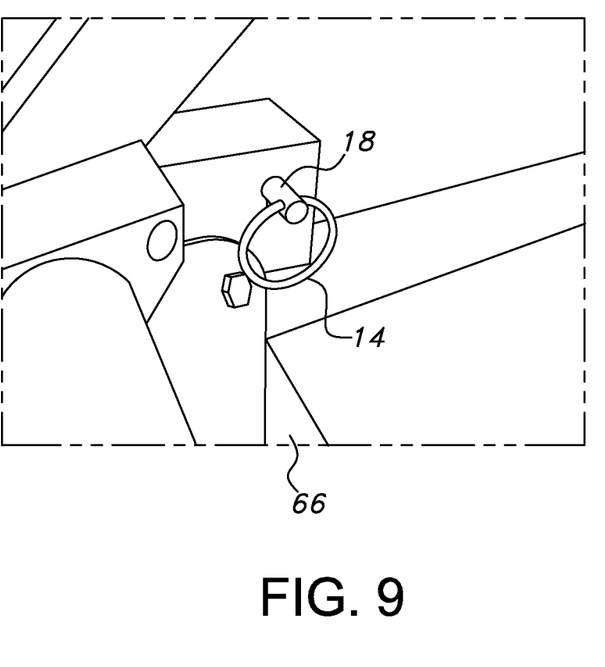
FIG. 9 is a detailed perspective view of a yoke arm housing about a yoke arm wherein the spring-loaded pin is positioned within the yoke arm housing in a second horizontal position to allow movement of the yoke arm.

As better illustrated in FIGS. 8 and 9, in order to place the yoke 48, 49, 50, 51 in operational position, the user will lift the yoke arms 68, 69, 70, 71 to the second position and secure them in place with a securing device, such as a cotter-pin (not shown) or a key ring 14 which engages a spring-loaded pin 18 that extends within the housing 19 of the yoke arm hinge 66 and that is sized to engage with any one of a plurality of slots 23 through the yoke arm 68. For storage and shipping yoke arms 68, 69, 70, 71 are pivoted to the first position and secured to the horizontal beams 109, 110 with releasable connectors, such as snaps 8 (shown in FIG. 1), straps (not shown), latches (not shown) or mating pressure points (not shown).

As shown in FIG. 7, the yokes 51 are suitably designed to accommodate and securely hold in place a stretcher poles 67 having a variety of thicknesses and/or geometrical cross-sections, with the standard stretcher pole 67 diameter being 1.5 inches and having a roughly circular cross-section viewed along the longitudinal axis. The yoke 51 may further comprise a hook (not shown), over-center latch clamp (not shown), or a strap 73 made of nylon, polypropylene, rubber, silicone, canvas or similar high-strength webbing, depending on user preference and requirements.

As best shown in FIG. 4, the platform 118 is configured for the attachment of a wide variety of standard operating table attachments, such as, but not limited to, one or more telescoping IV pole 80, armboard 90, surgical instrument trays 62, 63 77, a folding lower shelf 36 (shown in FIG. 1), a fluid containment sheet 61 (shown in FIG. 1), and other surgical or medical equipment. Optionally, on each end of the horizontal beams 109, 110 is a mounting fixture, such as hole 79 designed receive and adjustably secure a standard 0.5 inch or other diameter IV pole, light pole, or other 0.5 inch. One or a plurality of holes 79 having other diameters sized to receive any desired post (not shown) may also be provided about the perimeter of the platform 118. In one embodiment, on the side of the horizontal beam 109, 110 in communication with hole 79 is a threaded thumbscrew mounting bracket 78 that may be tightened or loosened to lock the IV pole 80 or other pole rigidly in place with a securing knob 82, such as in case of an abrupt upward or downward movement of the platform 118 while being transported in a land vehicle or aircraft. In another embodiment, stainless steel tie downs (not shown) are located at each corner 116 of the platform 118, individually rated to approx. 8,000-pound tensile strength.

Standard operating table attachments, such as folding equipment tray 62 may be mounted on in holes 79 provided about the perimeter of the platform 118, or may be proved with a slide rail shuttle 34 that engages with slotted side rails 117 formed or attached substantially along the length of the horizontal beams 109, 110. Attachments are held in place using holes 79, a tightening knob 88 on the slide rail shuttle (shown in FIG. 1), mounting arms 84, or on brackets (not shown) at the head end of the platform 118, or a combination thereof. One embodiment of the tray 62 is configured to support anesthetist's equipment 77 equipped with adjustable arms that are locked in place with a securing knob 83. Trays 62, 63, 77 may be configured to fold at a hinge 86 as desired to both conserve space and prevent damage when being transported before attachment to the platform 118. Trays 62, 63, 77 may desirably be made from stainless steel or other metal or reusable fiberglass trays. Brackets (now shown) may be provided to support a piece of medical equipment, such as, but not limited to, a ventilator, a vital signs monitor, a surgical piece of equipment, or an anesthetist piece of equipment.

FIG. 4 also shows optional armboards 90, which may be attached to the platform 118 in the same manner as trays 62, 63, 77. Preferably, armboards 90 are mounted on slide rail shuttles 34 and readily slide on the side rails 117 on the horizontal beams 109, 110, and optionally lock in position with a threaded screw knob 89. The armboards 90 can be oriented flush in line with the longitudinal axis of the platform 118 as shown in FIG. 1, or swivel outward or inward as shown in FIG. 4 at an angle relative to the beams 109, 110 utilizing a pivoting mechanism 92. A pivoting mechanism 92 allows the armboard 90 to be angled relative to the platform, between 0 and 180 degrees to support the patient's arm at whatever angle the surgeon wishes, or by swiveling out the surgeon's way entirely. This range includes all values and subranges therebetween. The armboard 90 may also be configured to angle up or down relative to the plane of the stretcher 113 using a sliding collar 94 adjustment. The armboard 90 may also be contoured to cradle the patient's arm. Optionally attached to each armboard 90 is, depending on use preference, either a VELCRO-type hook and loop fastener or a latching strap to restrain the patient's arm onto the armboard 90.

As shown in FIG. 1, a fluid containment sheet 61 made of PVC-coated fabric or comparable non-porous fabric may be suspended between the beams 109, 110 below the stretcher 113 on hooks attached proximate to each corner 100, 101, 102, 103 of the platform 118. The fluid containment sheet 61 contains bodily fluids and other materials spilling through the stretcher 113 before and during surgery. In a preferred embodiment shown best in FIG. 3, the fluid containment sheet 61 further comprises a drain 60 through which all such fluids are funneled into a collection container (not shown), such as a pan, tank, bag, or, preferably, a disposable bag filled with a mass of absorbent crystals.

FIG. 1 shows one embodiment of a folding lower shelf 36, which may be optionally attached to the platform 118. Folding lower shelf 36 may be configured such that it also acts as a reinforcing brace and structural member of the platform 118 when attached. Folding lower shelf 36 comprises an opposing pair of shelf bars 39 connected between support members 32, preferably connected longitudinally between support members 32 on the same side of opposing ends of the platform 118. The shelf bars 39 of the lower shelf 36 may be suitably made of 1 inch diameter aluminum tubing. Shelf bars 39 have a connecting link or hinge 52 and, similar to the two piece locking braces 2, serve to hold the opposing support members 32 rigidly in place. The folding lower shelf 36 further comprises a tear-resistant, flame retardant polymer fabric 37, such as double-extruded polyester fabric, stretched tightly between the shelf bars 39. Use of a fabric 37 to form the lower shelf 36 allows the fabric to be more easily carried as a folded or rolled fabric, rather than having a relatively large and cumbersome rigid lower shelf (not shown) to span the space created between the shelf bars 39. When disconnected from the support members 32 and folded in half at the hinge 52, the shelf bars 39 and fabric 37 can be rolled up together for transport or storage. The lower shelf 36 unfolds as shown and is attached by any suitable means, including a mounting bolt 38 in each of the four corners to a receiver bracket 42 with a retaining knob 47 on the inside of the support members 32 of the unitary platform 118. Steel inserts may be suitably installed in the receiver brackets 42 such that the mounting bolts 38 of the folding lower shelf 36 thread into steel rather than relatively soft aluminum, thus avoiding deformation caused by overtightening. The lower shelf 36 may be configured to desirably support up to approximately 500 pounds, including all values and subranges therebetween.

The configuration of the platform 118 may vary significantly. In one embodiment, horizontal beams 109, 110 may be 1 inch by 2 inch by ⅛ inch think aluminum tubing, such that it should be sufficiently rugged to stand up to heavy use in the field. The beams 109, 110 may have any cross section, such as, but not limited to, square, rectangle, I-beam, trapezoidal, hexagonal, triangular, oval, circular, rounded, or any combination thereof. Although any cross section is possible, it has been found that beams 109, 110 having rectangular or I-beam cross sections provide the best strength and nesting capabilities, while allowing for significant amounts of material to be removed as a weight-saving measure without sacrificing the requisite strength of the beams 109, 110. Material may be removed (and weight thereby reduced) by having a plurality of openings 12 in not only beams 109, 110, but also in substantially all structural elements of the platform 118, including beams 109, 110, submembers 111, 112, 98, 99, support members 32, leg extensions 43, 44, 45, 46, yoke arms 48, 49, 50, 51, cross-bars 3, 4 and locking braces 2. In one embodiment, the platform 118 will support at least 400 pounds without damage or permanent deflection. This range include all values and subranges therebetween. In one embodiment the platform 118 has been successfully test-loaded with over 600 pounds without damage or permanent deflection.

Any or all structural elements of the platform 118, including beams 109, 110, submembers 111, 112, 98, 99, support members 32, leg extensions 43, 44, 45, 46, yoke arms 48, 49, 50, 51, cross-bars 3, 4 and locking braces 2 may be made from any suitable material so long as it is sufficiently durable and operates as shown and described herein. Some exemplary materials include, but are not limited to, aluminum, steel, titanium, bronze, composite alloys or other sturdy metals, polymers, carbon fiber, plastic, ceramics, material composites and combinations thereof. In one embodiment, any or all of the structural elements of the platform 118, including beams 109, 110, submembers 111, 112, 98, 99, support members 32, leg extensions 43, 44, 45, 46, yoke arms 48, 49, 50, 51, cross-bars 3, 4 and locking braces 2 are resistant to corrosion. Additionally, all swiveling, sliding, and folding aluminum connections may be separated by ultra-low coefficient of friction virgin polytetrafluoroethylene (or Teflon®) or ultra-high-molecular-weight (UHMW) polyethylene spacers to prevent aluminum self-galling and seizing of mating surfaces, incorporate oil-impregnated bronze bushings, and held together with stainless steel bolts and deformed-thread self-locking nuts tightened to prevent play.

To facilitate the purpose of portability over large distances by a single individual which is a primary object of the invention, the platform 118 is preferably constructed from light-weight materials providing sufficient strength to be used as an operating table. Preferably, the unitary platform 118 weighs as little as possible. A preferred embodiment weight as little as about 45 pounds. When the unitary platform 118 is supplemented by the addition of optional equipment such as a lower shelf 36, armboards 90, and surgical instrument support trays 62, 63, 77, the combined weight of the platform 118 and optional standard operating table attachments may weigh only up to about 60 pounds. As already noted, the platform 118 and any of its components may be suitably made from any material, including metal aluminum, steel, titanium, bronze, allow composite, polymer, carbon fiber, plastic, or combinations thereof.

In one embodiment, the platform 118 is readily and quickly height-adjustable to provide a comfortable working height for surgeons of various heights and personal operating preferences. In one embodiment, the height of the platform 118 may be adjusted over a range of about 6 to 28 inches from the lower end of the support members 32 to the yokes 48, 49, 50, 51, which range includes all values and subranges therebetween. The height may be adjusted by adjusting the connection of leg extensions 43, 44, 45, 46 to support members 32 by making such connection at any one of the plurality of adjustment slots 96 positioned incrementally along the length of the leg extensions 43, 44, 45, 46. Any one of the support members 32 may be independently height adjustable from the other support members 32. The height of the platform 118 may be adjusted such that the entire platform may be raised or lowered uniformly (i.e., all support members 32 and leg extensions 43, 44, 45, 46 connected to have the same length), or one end may be raised or lowered, or one side may be raised or lowered as appropriate. Any means of making connections for the height adjustment may be used so long as it is sufficiently durable and has a raising and lowering function. Exemplary but non-limiting examples of height adjustment means include clamp, knob, friction fit, self-leveling ratchet type, screw type spring pin, and the like.

As discussed above in connection with FIGS. 7, 8 and 9, in addition to the height adjustment using the support members 32, the platform 118 may suitably include an independent adjustment means to allow for the raising or lowering of the stretcher 113. Independent adjustment members such as yoke arms 68, 69, 70, 71, allow for the adjustment of the height of either end of the stretcher 113 above the beams 109, 110. By raising the height of the yoke arms 68, 69 on one end of the platform 118 to a first height, but leaving the opposing yoke arms 70, 71 at a different second height, the stretcher 113 may be tilted up to 25 degrees from end to end independently of the platform 118, which range include all values and subranges therebetween. This independent adjustment suitably allows the movement of the patient into the "Trendelenburg" position, a common critical surgical procedure in which the patient is tilted head-down such that the patient's heart is higher than the brain.

FIG. 2 shows a side view of a portable field surgical platform 118 in a folded, upright configuration, according to the present invention. In this configuration, the platform 118 folds to fit into the space of a cube approximately 41" by 12" by 15", but the present article should not be limited by size, so long as it is sufficient to support a stretcher 113. This folded-up position is one position that allows for easy transport and stowage, for example, as it would be carried by one person manually, or in a land vehicle, emergency vehicle, ship, or aircraft.

FIG. 7 is a detailed view of one embodiment of a portable field surgical platform 118 wherein yoke 51 and yoke arm 70 are in a raised position. The stretcher 113 is dropped into place, and a metal hook (not shown) or folding strap 73 is placed over the stretcher pole 67 and fitted into a retaining bracket (not shown) on the back side of the yoke 51. In cases where of a metal hook is used (not shown), the latch clamp locks in an over-center position with a force that may, for example, be adjustable by self-locking nuts (not shown) on the clamp. This clamp can also be spring-loaded to automatically spring open when unlatched or closed when receiving the stretcher pole 67 should surgeons so desire. FIG. 7 shows one embodiment of the platform with the stretcher 113 locked in place using a strap 73, which may include one or more eyes, openings, or grommets to receive and engage a hook or post or it may include a VELCRO type closure, snaps, or buckle, or any combination thereof.

Although this invention has been disclosed and described in its preferred forms with a certain degree of particularity, it is understood that the present disclosure of the preferred forms is only by way of example and that numerous changes in the details of operation and in the combination and arrangement of parts may be resorted to without departing from the spirit and scope of the invention as hereinafter claimed.

I claim:

1. An apparatus for supporting a stretcher comprising:
   (a) a pair of horizontal beams, each horizontal beam comprising:
      (i) first and second submembers, each submember having an inboard end and outboard end;
      (ii) a pivoting hinge connecting the inboard ends of the submembers, said pivoting hinge allowing the first and second submembers to move between a first unfolded position in which the submembers align substantially straight and parallel, and a second folded position in which the submembers lie substantially parallel to each other and define an internal space between the submembers;
   (b) one or more yokes connected to said horizontal beam, said yokes adapted to receive a stretcher;
   (c) said yokes having an independently adjustable height;
   (d) a plurality of support members, in outwardly canted positions, attached to the horizontal beams;
   (e) a pair of folding, connected cross-bars connecting a first support member to a second support member thereby maintaining the horizontal beams substantially in parallel when the apparatus is in the first unfolded position; and
   (f) each of said cross-bars having a hinge point to allow inward motion of the opposing pairs of support members to collapse the cross-bars until the cross-bars lie substantially parallel with each other and with the support members.

2. The apparatus of claim 1 wherein support members are hingedly connected proximate to the outboard ends of the submembers.

3. The apparatus of claim 2 wherein the hinged connections independently allow the hingedly connected submembers and support members to move between a first position at which the hingedly connected submember and support member are substantially parallel to one another and a second position at which the hingedly connected submember and support member are at an angle of greater than about 90 degrees but less than about 105 degrees from one another.

4. The apparatus of claim 1 wherein each support member has an independently adjustable length.

5. The apparatus of claim 1 wherein each yoke is connected to a corresponding horizontal beam by a yoke arm attached between the yoke and the corresponding horizontal beam.

6. The apparatus of claim 5 wherein said yoke arms are pivotably attached proximate to the outboard ends of the horizontal beams so that the yoke arm may be pivoted to a first position lying flat, lengthwise along the beam when the platform is in the folded position, and pivoted to a second position substantially perpendicular to the horizontal beams when the platform is in the unfolded position.

7. The apparatus of claim 1 further comprising a plurality of mounts for surgical accessories.

8. The apparatus of claim 1 having a plurality of platform corners and further comprising tie down means at each platform corner.

9. The apparatus of claim 1 wherein the support members are equipped with off-center mounting holes.

10. The apparatus of claim 1 wherein at least one support member further comprises a non-skid, self-leveling foot.

11. The apparatus of claim 1 wherein at least one support member further comprises a wheel.

12. The apparatus of claim 1 wherein said apparatus is configurable to the second folded position, the apparatus in such folded configuration measuring 41"×12"×15".

13. The apparatus of claim 1 wherein said apparatus consists of a single, unitary piece apparatus and may be configurable between the first unfolded position and the second folded position without the use of any tools or the need to connect any loose pieces.

14. The apparatus of claim 1 further comprising a plurality of mounting brackets for an intravenous pole.

15. The apparatus of claim 1 further comprising side rails capable of accepting all surgical accessories that mount on 5/16 inch by 1 1/8 inch rails.

16. The apparatus of claim 1 wherein at least one support member further comprises a leg extension capable of being interchanged with a wheel.

17. The apparatus of claim 7 further comprising a standard operating table attachment selected from the group consisting of a pole-mounted swiveling cantilevered surgical instrument tray, a side-mounted miscellaneous surgical items tray, an end-mounted anesthetist's gear tray, an end-mounted, multi-positional bracket to support a piece of medical equipment, an armboard, an antimicrobial-vinyl fluid containment sheet, and a lower shelf.

18. The apparatus of claim 7 wherein said mounts further comprise stainless steel bolts and deformed thread self-locking nuts.

19. The apparatus of claim 1 wherein
(a) one or more of the connections selected from the group consisting of the connection between one or more of the pivoting hinges and one or more of the submembers, the connection between one or more of the horizontal beams and one or more of the yokes, the attachment between one or more of the horizontal beams and one or more of the support members and the connection between one or more of the cross-bars and one or more of the support members
(b) further comprises a spacer, said spacer selected from the group consisting of an ultra-low coefficient of friction virgin polytetrafluoroethylene spacer and a ultra-high-molecular-weight polyethylene spacer.

20. An apparatus for supporting a stretcher comprising:
(a) a pair of horizontal beams, each horizontal beam comprising:
(i) first and second submembers, each submember having an inboard end and outboard end;
(ii) a pivoting hinge connecting the inboard ends of the submembers, said pivoting hinge allowing the first and second submembers to move between a first unfolded position in which the submembers align substantially straight and parallel, and a second folded position in which the submembers lie substantially parallel to each other and define an internal space between the submembers;
(b) one or more yokes connected to said horizontal beam, said yokes adapted to receive a stretcher;
(c) a plurality of support members attached to the horizontal beams, said support members each having an independently adjustable length; and
(d) a pair of folding, connected cross-bars connecting a first support member to a second support member thereby maintaining the horizontal beams substantially in parallel when the apparatus is in the first unfolded position.

21. An apparatus for supporting a stretcher comprising:
(a) a pair of horizontal beams, each horizontal beam comprising:
(i) first and second submembers, each submember having an inboard end and outboard end;
(ii) a pivoting hinge connecting the inboard ends of the submembers, said pivoting hinge allowing the first and second submembers to move between a first unfolded position in which the submembers align substantially straight and parallel, and a second folded position in which the submembers lie substantially parallel to each other and define an internal space between the submembers;
(b) one or more yokes connected to said horizontal beam, said yokes adapted to receive a stretcher;
(c) said yokes each having an independently adjustable height; and
(d) a plurality of support members attached to the horizontal beams;
(e) a pair of folding, connected cross-bars connecting a first support member to a second support member thereby maintaining the horizontal beams substantially in parallel when the apparatus is in the first unfolded position.

22. The apparatus of claim 21 wherein each yoke is connected to a corresponding horizontal beam by a yoke arm attached between the yoke and the corresponding horizontal beam.

23. The apparatus of claim 22 wherein said yoke arms are pivotably attached proximate to the outboard ends of the horizontal beams so that the yoke arm may be pivoted to a first position lying flat, lengthwise along the beam when the platform is in the folded position, and pivoted to a second position substantially perpendicular to the horizontal beams when the platform is in the unfolded position.

24. An apparatus for supporting a stretcher comprising:
(a) a pair of horizontal beams, each horizontal beam comprising:
(i) first and second submembers, each submember having an inboard end and outboard end;
(ii) a pivoting hinge connecting the inboard ends of the submembers, said pivoting hinge allowing the first and second submembers to move between a first unfolded position in which the submembers align substantially straight and parallel, and a second folded position in which the submembers lie substantially parallel to each other and define an internal space between the submembers;
(b) one or more yokes connected to said horizontal beam, said yokes adapted to receive a stretcher;
(c) a plurality of support members attached to the horizontal beams;
(d) wherein the support members are outward-canted and equipped with off-center mounting holes; and
(e) a pair of folding, connected cross-bars connecting a first support member to a second support member thereby maintaining the horizontal beams substantially in parallel when the apparatus is in the first unfolded position.

25. An apparatus for supporting a stretcher comprising:
(a) a pair of horizontal beams, each horizontal beam comprising:
  (i) first and second submembers, each submember having an inboard end and outboard end;
  (ii) a pivoting hinge connecting the inboard ends of the submembers, said pivoting hinge allowing the first and second submembers to move between a first unfolded position in which the submembers align substantially straight and parallel, and a second folded position in which the submembers lie substantially parallel to each other and define an internal space between the submembers;
(b) one or more yokes connected to said horizontal beam, said yokes adapted to receive a stretcher;
(c) a plurality of support members attached to the horizontal beams;
(d) a pair of folding, connected cross-bars connecting a first support member to a second support member thereby maintaining the horizontal beams substantially in parallel when the apparatus is in the first unfolded position; and
(e) at least one side rail capable of accepting all surgical accessories that mount on $5/16$ inch by $1\tfrac{1}{8}$ inch rails.

* * * * *